(12) United States Patent
Kimizuka et al.

(10) Patent No.: US 7,041,842 B2
(45) Date of Patent: May 9, 2006

(54) FERROCENE-CONTAINING, ORGANIC GELLING COMPOUND, AND GEL AND CAST FILM USING THE SAME

(75) Inventors: Nobuo Kimizuka, Fukuoka (JP); Noriyuki Matsumoto, Fukuoka (JP); Kazuhiro Kagawa, Wako (JP); Hiroshi Yokobayashi, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/506,961

(22) PCT Filed: Mar. 4, 2003

(86) PCT No.: PCT/JP03/02505

§ 371 (c)(1),
(2), (4) Date: Mar. 22, 2005

(87) PCT Pub. No.: WO03/074540

PCT Pub. Date: Sep. 12, 2003

(65) Prior Publication Data

US 2005/0222277 A1 Oct. 6, 2005

(30) Foreign Application Priority Data

Mar. 7, 2002 (JP) .............................. 2002-062034

(51) Int. Cl.
*C07F 17/02* (2006.01)
*C08J 3/02* (2006.01)
(52) U.S. Cl. ...................... 556/145; 556/144; 516/102
(58) Field of Classification Search ................ 556/144, 556/145; 516/102
See application file for complete search history.

(56) References Cited

FOREIGN PATENT DOCUMENTS

JP 05-103974 4/1993

(Continued)

OTHER PUBLICATIONS

Appoh et al., Macromolecules, vol. 38, No. 18, pp. 7562-7570 (2005).*

(Continued)

*Primary Examiner*—Porfirio Nazario-Gonzalez
(74) *Attorney, Agent, or Firm*—Lahive & Cockfield, LLP; Anthony A. Laurentano, Esq.

(57) ABSTRACT

A ferrocene-containing, organic gelling compound represented by the following general formula (I):

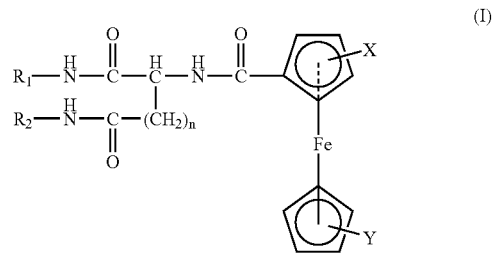

wherein $R_1$ and $R_2$ represent the same or different alkyl groups having 2 or more carbon atoms or alkyl groups containing at least one ether bond, X and Y independently represent a hydrogen atom or a substituent, and n represents an integer of 1 or 2, and a gel and a cast film using the compound.

10 Claims, 10 Drawing Sheets

FOREIGN PATENT DOCUMENTS

| | | |
|---|---|---|
| JP | 06-235812 | 8/1994 |
| JP | 07-068156 | 3/1995 |
| JP | 07-151727 | 6/1995 |
| JP | 08-245672 | 9/1996 |
| JP | 08-327584 | 12/1996 |
| JP | 11-169393 | 6/1999 |
| JP | 2001-085075 | 3/2001 |
| JP | 2001-226376 | 8/2001 |

OTHER PUBLICATIONS

Li, Xue-Mei et al., "Formation of gold colloids using thioether derivatives as stabilizing ligands," Journal of Materials Chemistry, 2001, vol. 11, No. 7, pp. 1919 to 1923.

* cited by examiner

1 μm 500 nm

FERROCENE-CONTAINING, ORGANIC GELLING COMPOUND, AND GEL AND CAST FILM USING THE SAME

RELATED APPLICATIONS

This application is a 35 U.S.C. 371 national stage filing of International Application No. PCT/JP03/02505, filed 04 Mar. 2003, which claims priority to Japanese Patent Application No. 2002-62034 filed on 07 Mar. 2002 in Japan. The contents of the aforementioned applications are hereby incorporated by reference.

FIELD OF THE INVENTION

The present invention relates to a novel, ferrocene-containing, organic gelling compound, and a gel and a cast film comprising such a compound.

BACKGROUND OF THE INVENTION

Ferrocene derivatives (compounds and electroconductive polymers containing ferrocene groups) have been used in various applications utilizing electroconductivity. For example, JP 5-103974 A, JP 6-235812 A and JP 7-68156 A disclose methods of using the ferrocene derivatives as surfactants (micelle-forming agents) in electrochemical processes for efficiently producing organic films usable for electronic materials such as color filters.

Further, known applications of redox layers comprising the ferrocene derivatives include an enzyme electrode composition comprising a resin and an electroconductive enzyme prepared by modifying an enzyme with a mediator of a ferrocene derivative (see JP 7-151727 A); an ion-selective electrode using a monolayer membrane comprising a particular ferrocene-containing compound as an intermediate layer between a metal electrode and an ion-sensitive membrane (see JP 8-327584 A); a threading intercalator comprising a particular ferrocene-containing compound, which is combined with an electrochemical analysis device to form a kit for electrochemically detecting DNA fragment samples (see JP 2001-226376 A); etc.

JP 8-245672 A discloses a liquid crystal compound of a particular ferrocene derivative with excellent orientation. Further, JP 2001-85075 A discloses a method of using an electroconductive polymer comprising a cross-linked polymer impregnated with a ferrocene derivative and a solvent in an electrolyte layer of a photoelectric conversion device, thereby providing a photoelectric conversion device higher in photoelectric conversion efficiency than conventional ones.

As described above, the ferrocene derivatives can be used in various applications. In recent years, high-electroconductivity polymers useful for electrochemically controllable gel actuators have been demanded. For example, JP 11-169393 A discloses an artificial muscle, which comprises a formed solid electrolyte and a polyaniline film formed thereon in an insulated state, so that it can be freely deformed in a predetermined direction by the difference of potential applied to the polyaniline film.

Electroconductive ferrocene-containing polymers are mainly those having ferrocene groups connected to polyethylene glycol as described in JP 5-103974 A, JP 6-235812 A and JP 7-68156 A, and those having cross-linked polymers impregnated with ferrocene derivatives as described in JP 2001-85075 A. These electroconductive polymers have limited ferrocene concentration, thereby showing insufficient electroconductivity.

To increase the ferrocene concentrations of the ferrocene-containing electroconductive polymers, the ferrocene derivatives preferably have associability (self-organizing properties), particularly gelling properties. When ferrocene derivatives having the gelling properties are formed into gels or cast films, it is expected that they have increased ferrocene concentration. However, such ferrocene derivatives having gelling properties are not described in the above prior art references.

OBJECT OF THE INVENTION

Accordingly, an object of the present invention is to provide a ferrocene-containing, organic gelling compound, and a gel and a cast film using such a gelling compound.

DISCLOSURE OF THE INVENTION

As a result of intense research in view of the above object, based on a conventionally known molecular design of synthetic bilayer membranes, by which a bilayer membrane of an amphiphile having a hydrophobic moiety and a hydrophilic moiety can be grown to a gel-forming fibrous structure, one of the gel-forming patterns, the inventors have found that a novel organic compound having a basic skeleton comprising a ferrocene group, an amino acid amide, and an alkyl group with or without at least one ether bond has a function of gelling an organic solvent or an ionic liquid. The present invention has been accomplished by this finding.

Thus, the ferrocene-containing, organic gelling compound of the present invention is represented by the general formula (I):

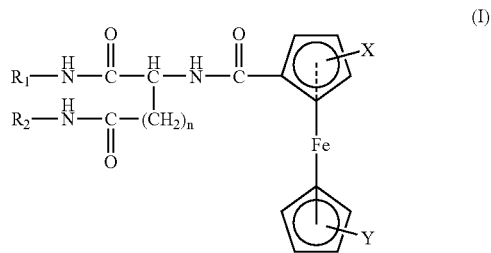

wherein $R_1$ and $R_2$, which may be the same or different, independently represent an alkyl group having 2 or more carbon atoms or an alkyl group containing at least one ether bond, X and Y independently represent a hydrogen atom or a substituent, and n represents an integer of 1 or 2.

The ferrocene-containing, organic gelling compound of the general formula (I) is preferably represented by the following formula (II):

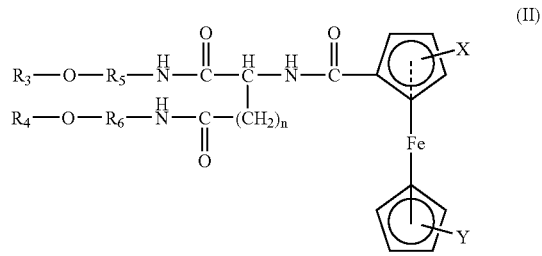

wherein $R_3$ and $R_4$, which may be the same or different, independently represent an alkyl group having 2 or more carbon atoms, $R_5$ and $R_6$, which may be the same or different, independently represent an alkylene group having 2 to 20 carbon atoms, X and Y independently represent a hydrogen atom or a substituent, and n represents an integer of 1 or 2. The gelling compound is more preferably represented by the following formula (III):

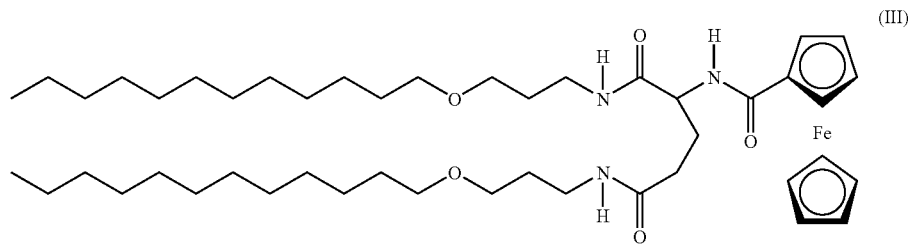

(III)

The present invention also provides a gelling agent comprising the gelling compound represented by the general formula (I), which can convert an organic solvent or an ionic liquid to a gel, and an organogel and an ionogel (a gel of an ionic liquid) comprising the gelling compound represented by the general formula (I). The organic solvent for forming a gel with the gelling compound represented by the general formula (I) is preferably acetonitrile, and the ionic liquid for forming a gel by the gelling compound is preferably N-methyl-N'-methoxymethylimidazolium bromide.

The present invention further provides a cast film obtained by casting the gelling compound represented by the general formula (I).

The ferrocene-containing, organic gelling compound of the present invention has two long hydrophobic chains (alkyl chains and/or alkyl chains containing at least one ether bond) for excellent molecular orientation, and three amide groups causing their molecules to interact with each other by hydrogen bonding to form a network structure. Therefore, the gelling compound can convert the organic solvent or the ionic liquid to a gel. In the gel comprising the ferrocene-containing, organic gelling compound of the present invention, the gelling compound molecules are associated with a certain orientation with the ferrocene groups integrated at a high concentration. Thus, electrons move efficiently between the ferrocene groups, so that the gel shows excellent electroconductivity (or redox properties).

THE BEST MODE FOR CARRYING OUT THE INVENTION

[1] Ferrocene-Containing, Organic Gelling Compound

Figure 1:
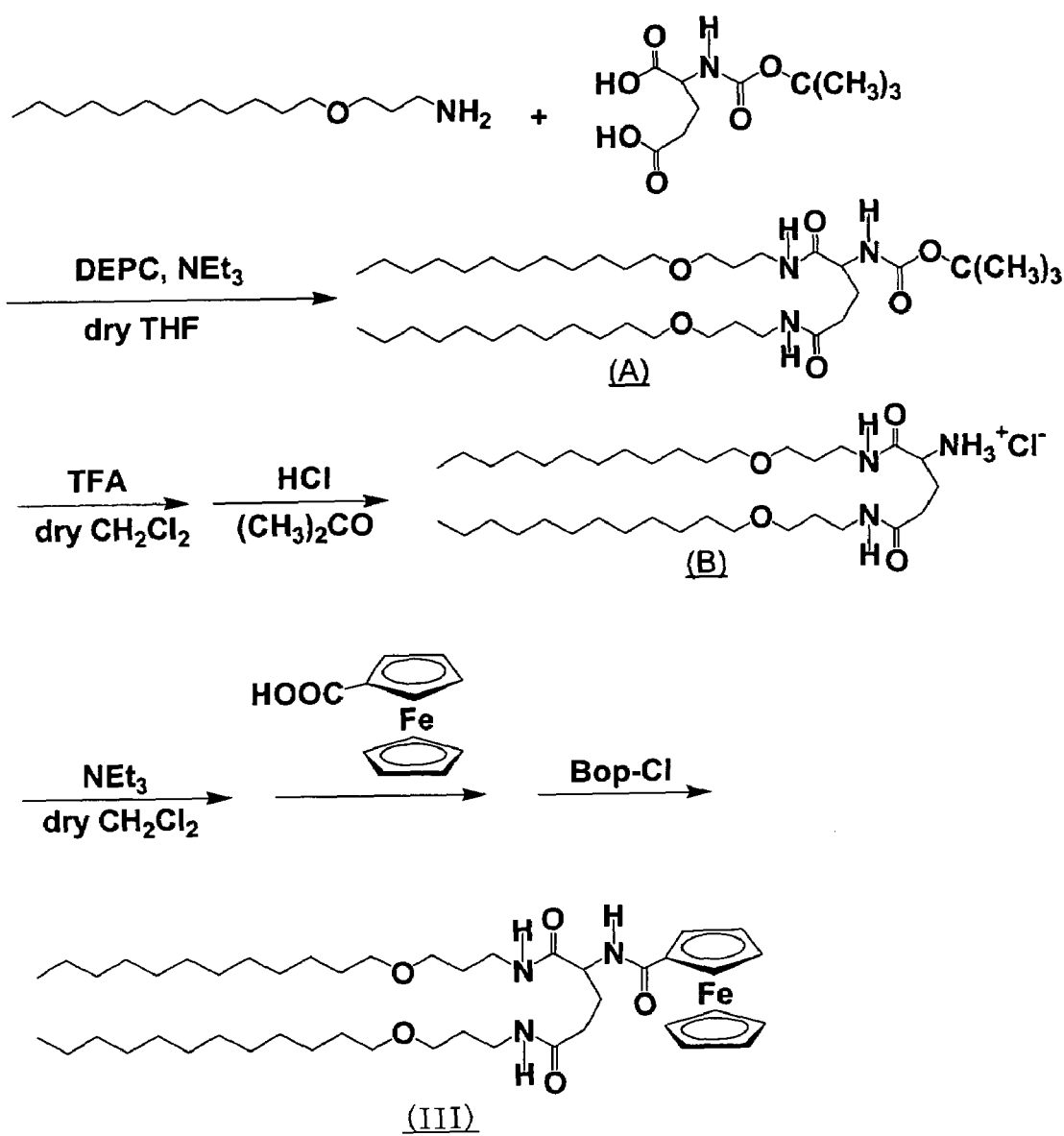
FIG. 1 is a flow chart showing a synthesis scheme of a ferrocene-containing, organic gelling compound (III)

The ferrocene-containing, organic gelling compound of the present invention, which is represented by the general formula (I):

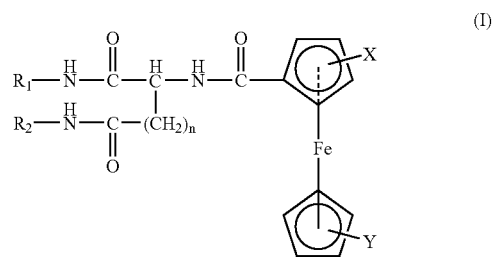

wherein $R_1$ and $R_2$, which may be the same or different, independently represent an alkyl group having 2 or more carbon atoms or an alkyl group containing at least one ether bond, X and Y independently represent a hydrogen atom or a substituent, and n represents an integer of 1 or 2, has a function of converting a particular organic solvent or ionic liquid to a gel. This appears to be due to the fact that the gelling compound represented by the general formula (I) has such a chemical structure that it has two long hydrophobic chains (alkyl chains and/or alkyl chains containing at least one ether bond) for excellent molecular orientation, and that their molecules are easily interacted with each other (or easily associated) by hydrogen bonding between amide groups to form a network structure. The gelling compound of the general formula (I) is dispersible in organic solvents because of hydrophobic chains (alkyl chains and/or alkyl chains containing at least one ether bond). Further, the gelling compound of the general formula (I) has no electric charge in molecules, so that it is well dispersible in ionic liquids, too. Thus, the gelling compound has a function of gelling organic solvents and ionic liquids, which have proper polarity making the gelling compound solvatable to such an extent that it maintains associability (self-organizing properties).

Observation by an atomic force microscope (AFM), a transmission electron microscope (TEM), a dark-field optical microscope, etc. reveals that a gel produced by placing the gelling compound of the general formula (I) in such an organic solvent or an ionic liquid has a typical, fibrous, entangled gel structure. The gelling compound of the general formula (I) is so associative that it can easily be formed into a film by casting a solution or dispersion of the gelling compound in a solvent on an electrode substrate.

To achieve the above properties, each of $R_1$ and $R_2$ in the general formula (I) is an alkyl group having 2 or more carbon atoms or an alkyl group containing at least one ether bond. When the alkyl group or the alkyl group containing at least one ether bond is an excessively long chain, the gelling compound cannot convert the organic solvent or the ionic liquid with the above polarity to a gel, but is dissolved or precipitated therein. Thus, both of the alkyl group and the alkyl group containing at least one ether bond preferably have 40 carbon atoms or less. Though $R_1$ and $R_2$ may be the same or different groups, they are preferably the same alkyl groups or the same alkyl groups containing at least one ether bond.

The ferrocene-containing, organic gelling compound of the general formula (I) is preferably represented by the following formula (II):

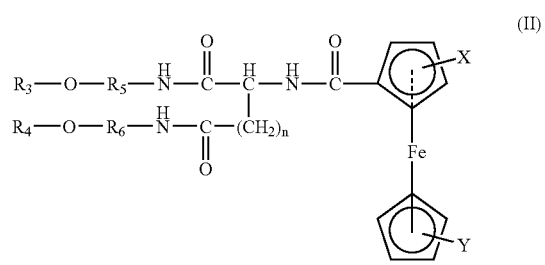

wherein $R_3$ and $R_4$ represent the same or different alkyl groups having 2 or more carbon atoms, $R_5$ and $R_6$ represent the same or different alkylene groups having 2 to 20 carbon atoms, X and Y independently represent a hydrogen atom or a substituent, and n represents an integer of 1 or 2.

$R_3$ and $R_4$ in the formula (II) are preferably alkyl groups having 2 or more carbon atoms. Thus, $R_3$ and $R_4$ may be represented by the formula $CH_3$—$(CH_2)_a$—, in which a is 1 or more. When the alkyl groups are excessively long chains, the gelling compound cannot convert the organic solvent or the ionic liquid with the above polarity to a gel, but is dissolved or precipitated therein. The alkyl groups preferably have 30 or less carbon atoms. Though $R_3$ and $R_4$ may be the same or different groups, they are preferably alkyl groups having the same lengths.

$R_5$ and $R_6$ in the formula (II) are preferably alkylene groups having 2 to 20 carbon atoms. Thus, $R_5$ and $R_6$ may be represented by the formula —$(CH_2)_b$—, wherein b is 2 to 20. Though $R_5$ and $R_6$ may be the same or different groups, they are preferably alkylene groups having the same lengths. The total number of carbon atoms is preferably 40 or less both in $R_3$ and $R_5$ and in $R_4$ and $R_6$. When the total number of carbon atoms is more than 40, the gelling compound cannot convert the organic solvent or the ionic liquid with the above polarity to a gel, but is likely to be dissolved or precipitated therein.

The ferrocene-containing, organic gelling compound of the general formula (I) is more preferably represented by the following formula (III):

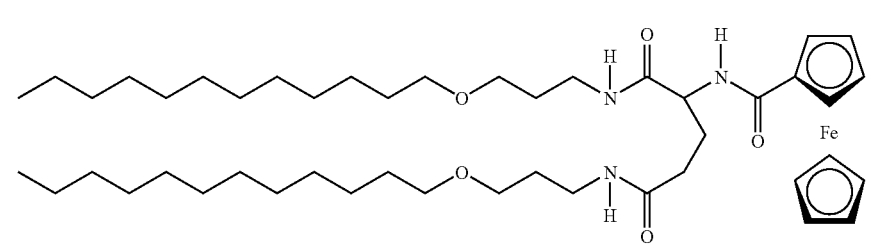

A further structural feature of the ferrocene-containing, organic gelling compound represented by the general formula (I) is that it has an amino acid amide in its skeleton. The amino acid amide is derived from glutamic acid amide or aspartic acid amide.

The gelling compound molecule of the general formula (I) has 3 amide groups because of the amino acid amide in its skeleton. The amide groups interact with each other by hydrogen bonding to accelerate the association of the gelling compound molecules, thereby forming a network structure easily.

A still further structural feature of the ferrocene-containing, organic gelling compound represented by the general formula (I) is that it has a ferrocene group. The ferrocene group has such redox activity that the organic gelling compound has electroconductivity. X and Y independently represent a hydrogen atom or a substituent. Examples of the substituents include a methyl group, a carboxyl group, a hydroxymethyl group, etc. Though the ferrocene group is hydrophobic, it is coupled with a hydrophobic moiety with high molecular orientation, which is the alkyl chain or the alkyl chain containing at least one ether bond, thereby making the gelling compound of the general formula (I) amphiphilic, which determines orientation when the gelling compound molecules are associated and thus makes it easy to form a bilayer membrane structure.

The ferrocene-containing, organic gelling compound represented by the general formula (I) can be produced by various synthesis methods. In simple terms, the gelling compound having three amide groups and one ferrocene group may be produced by the steps of reacting a primary amine having an alkyl group or an alkyl group containing at least one ether bond, which corresponds to $R_1$ and $R_2$, with two carboxyl groups of an amino acid with a protected amino group to form two amide bonds; removing the protecting group; and reacting the deprotected product with a ferrocene having a carboxylic acid group to form a ferrocene moiety. For example, the gelling compound represented by the above formula (III) may be synthesized according to the scheme of FIG. 1.

[2] Gelling

The ferrocene-containing, organic gelling compound of the general formula (I) can convert particular organic solvents and ionic liquids to gels. The organic solvents for gelation include acetonitrile, etc. The ionic liquids for gelation include N-methyl-N'-methoxymethylimidazolium bromide represented by the following formula (IV):

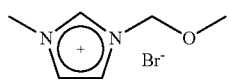

(IV)

The ionic liquid of the formula (IV) may be synthesized by a method disclosed in Japanese Patent Application No. 2000-184298, etc.

The gel may be formed by dispersing or dissolving the gelling compound of the general formula (I) in the organic solvent or the ionic liquid, and by leaving the resultant dispersion or solution at room temperature. The concentration of the dispersion and the solution is preferably 5 to 100 mM, more preferably 10 to 50 mM. The dispersing or dissolving step may be conducted with ultrasonic irradiation or heating, if necessary. In the case of dissolving the gelling compound while heating, the resultant solution is preferably cooled with ice to obtain a rigid gel immediately after the dissolving step.

In the gel comprising the ferrocene-containing, organic gelling compound of the general formula (I), the gelling compound molecules are associated with each other with a certain orientation, and the ferrocene groups are integrated at a high concentration, so that electrons are efficiently transferred between the ferrocene groups. Thus, the gels of the present invention have excellent redox properties, usable for electrochemically controllable gel actuators, electrolyte layers of photoelectric conversion devices, redox layers of enzyme electrodes (immobilization layers of enzyme-immobilized electrodes), etc. Particularly the ionogels prepared from the ionic liquids are promising as solid electrolytes in batteries. Further, it is likely that the gels can be used as materials for light-driven gel actuators by including photosensitizers such as ruthenium tris(bipyridine) complexes.

[3] Formation of Cast Film

The ferrocene-containing, organic gelling compound of the present invention represented by the general formula (I) has such excellent dispersibility in various organic solvents that they can be dissolved or dispersed therein. Examples of the organic solvents include alcohols such as methanol and ethanol; ketones such as acetone; esters such as ethyl acetate; furan compounds such as tetrahydrofuran; aromatic solvents such as benzene, toluene, and xylene; aliphatic solvents such as hexane and methylcyclohexane; chlorine-containing organic solvents such as chloroform, chlorocyclohexane, and carbon tetrachloride; etc.

The gelling compound of the general formula (I) can be easily formed into a cast film by the steps of dissolving or dispersing the gelling compound having associability in the organic solvent at an appropriate concentration; casting the resultant liquid on an electrode substrate; and evaporating the organic solvent. In the resultant cast film, the gelling compound molecules are associated with a certain orientation, and the ferrocene groups are integrated at a high concentration. Because of excellent redox properties, the cast film is usable for intermediate layers between electrode substrates and ion-sensitive membranes, thin display devices, etc.

The present invention will be described in more detail below with reference to Examples without intention of restricting the scope of the present invention.

EXAMPLE 1

The ferrocene-containing, organic gelling compound represented by the above formula (III) was produced according to the reaction scheme shown in FIG. 1.

(1) Synthesis of Compound (A)

4.3 g (17.8 mmol) of distilled 3-lauryloxypropyl-1-amine (available from Acros Organics, Mw 243.43), 2.0 g (8.1 mmol) of t-butyloxycarbonyl-L-glutamic acid (Boc-L-Glu-OH, available from Kokusan Chemical Co., Ltd., Mw 247.11), and 1.8 g (17.8 mmol) of distilled triethylamine (available from Kishida Chemical Co., Ltd., Mw 101.6) were introduced into a 200-ml, short-neck flask, and dissolved in 150 ml of dry tetrahydrofuran (THF). 2.9 g (17.8 mmol) of diethyl phosphorocyanidate (DEPC, available from Aldrich, Mw 163.11) was slowly added to the ice-cooled solution while stirring, and the reaction mixture was stirred under ice cooling for 30 minutes and then at room temperature for 3 days. THF was then distilled off under reduced pressure to obtain a pale-yellow oily residue. The residue was dissolved in chloroform, and a 5-weight-% aqueous sodium carbonate solution was added thereto and shaken twice, and ion-exchanged water was then added thereto and shaken twice. A chloroform phase was isolated, and anhydrous sodium sulfate was added thereto and stirred to remove residual water. Sodium sulfate was removed by suction filtration, chloroform was distilled off under reduced pressure, and the pale-yellow solid residue was recrystallized from acetone to obtain 3.4 g of colorless powder of Compound (A) at a yield of 60.2%.

(2) Synthesis of Compound (B)

3.4 g (4.9 mmol) of Compound (A) (Mw 698.07) was dissolved in 100 ml of dry dichloromethane, and trifluoroacetic acid (TFA, available from Kishida Chemical Co., Ltd., Mw 114.02) was added thereto at a concentration of 20% by weight while stirring. The resultant mixture was stirred at room temperature overnight. Trifluoroacetic acid and dichloromethane were then distilled off under reduced pressure to obtain an oily residue, which was dissolved in about 50 ml of acetone. 1 ml of a 35-weight-% aqueous hydrochloric acid was added thereto while cooling with ice, and precipitates were isolated by filtration. The precipitates were recrystallized from ethyl acetate twice, to obtain 1.40 g of colorless powder of Compound (B) at a yield of 40.9%.

(3) Synthesis of Ferrocene-Containing, Organic Gelling Compound (III)

Figure 2:
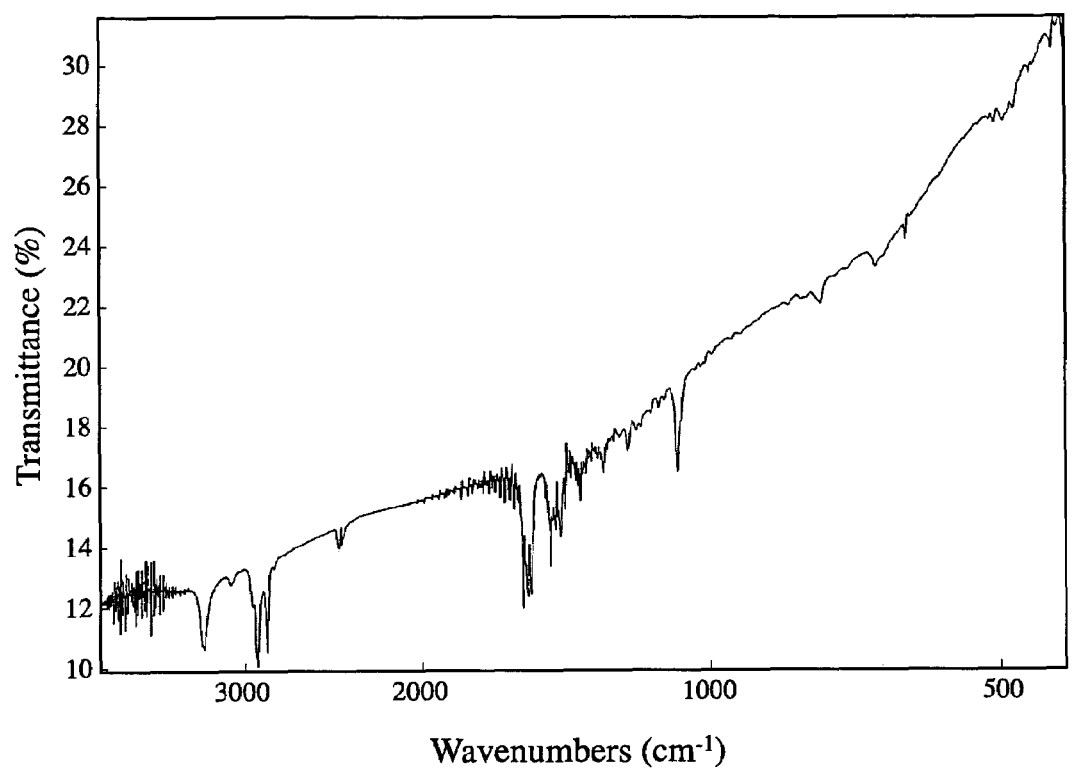
FIG. 2 is a graph showing an FT-IR spectrum of the ferrocene-containing, organic gelling compound (III)

1.0 g (1.58 mmol) of the above Compound (B) (Mw 634.12) and 0.20 g (1.8 mmol) of triethylamine (available from Kishida Chemical Co., Ltd., Mw 101.6) were dissolved in chloroform, and ion-exchanged water was added thereto with the resulting mixture shaken. A chloroform phase was isolated and dried overnight over anhydrous sodium sulfate. Sodium sulfate was removed by filtration, and chloroform was distilled off under reduced pressure. The residue was then dissolved in dry dichloromethane, and 0.20 g (1.8 mmol) of distilled triethylamine (Mw 101.6) and 0.40 g (1.73 mmol) of ferrocenecarboxylic acid (available from Aldrich, Mw 230.05) were added thereto. 0.44 g (1.73 mmol) of N,N-bis(2-oxo-3-oxazolidinyl)-phosphinic chloride (Bop-Cl, available from Tokyo Kasei Kogyo Co., Ltd., Mw 254.56) was added to the reaction mixture while stirring under ice-cooling, and then stirred under ice-cooling for 30 minutes and at room temperature for 3 days. Dichloromethane was distilled off under reduced pressure to obtain a residue, which was dissolved in chloroform. A 5-weight-% aqueous sodium hydrogen carbonate solution was added thereto and shaken. An aqueous hydrochloric acid solution (pH: 4 to 5) was then added to the mixture and shaken, and ion-exchanged water was added thereto and shaken. A chloroform phase was then isolated, and dried overnight over anhydrous sodium sulfate. Sodium sulfate was removed by suction filtration, and chloroform was distilled off under reduced pressure. Chromatography with a silica gel column using a developing solvent of $CHCl_3$ indicated that the residue contained four components, first to fourth components in the order of elution. The first and second components (unidentified) were removed, and the other components were subjected to a silica gel column chromatography using a developing solvent of $CHCl_3/CH_3OH$ (10/1), to isolate the third component [ferrocene-containing, organic gelling compound (III) represented by the formula (III)]. The third component was recrystallized from hexane to obtain 0.4 g of a pale-yellow solid at a yield of 31%. The melting point of the product was 82.1 to 83.5° C. The product was identified by an FT-IR analysis. The results of the FT-IR analysis are shown in FIG. 2 and Table 1.

TABLE 1

| FT-IR assignment | |
|---|---|
| $v$ (cm$^{-1}$) | Assignment |
| Around 3,300 | Amide, $v_{NH}$ |
| 2,925 and 2,854 | Methylene, $v_{CH}$ |
| Around 1,654 | Amide, $v_{C=O}$ |
| Around 1,535 | Amide, $\sigma_{NH}$ |

Figure 3:
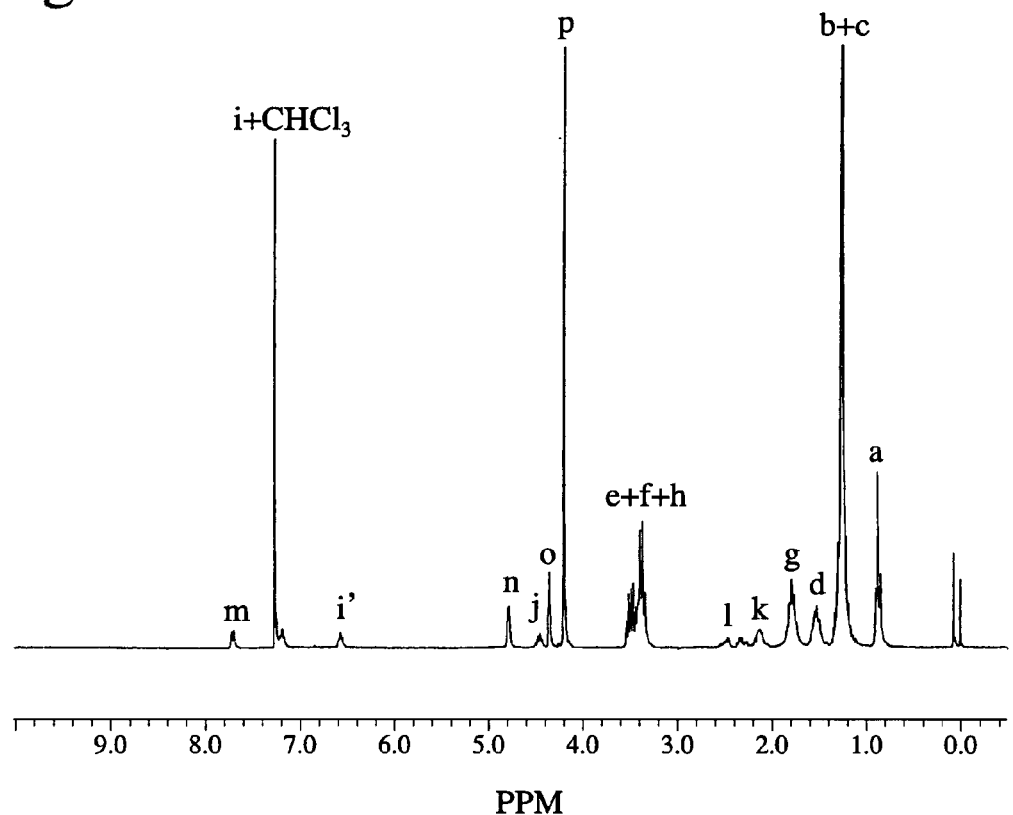
FIG. 3 is a graph showing a $^1$H-NMR spectrum of the ferrocene-containing, organic gelling compound (III)

Further, $^1$H-NMR analysis of the product was carried out. The results are shown in FIG. 3 and Table 2. Symbols used in Table 2 for the hydrogen atoms are shown in the following formula (V).

TABLE 2

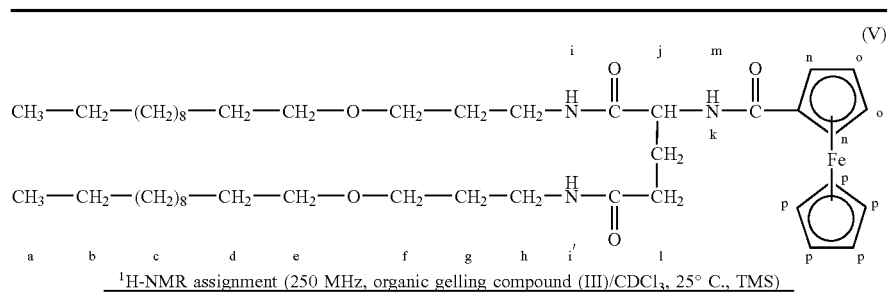

(V)

$^1$H-NMR assignment (250 MHz, organic gelling compound (III)/CDCl$_3$, 25° C., TMS)

| δ (ppm) | Theoretical Value | Observed Value | Assignment | Peak Splitting |
|---|---|---|---|---|
| 0.7 to 0.9 | 6 H | 6.0 H$^{(1)}$ | a | m |
| 1.1 to 1.4 | 36 H | 34.9 H | b + c | m |
| 1.4 to 1.7 | 4 H | 4.2 H | d | m |
| 1.7 to 1.9 | 4 H | 4.2 H | g | m |
| 2.0 to 2.2 | 2 H | 1.8 H | k | m |
| 2.2 to 2.6 | 2 H | 1.6 H | l | m |
| 3.3 to 3.6 | 12 H | 11.1 H | e + f + h | m |
| 4.1 to 4.3 | 5 H | 4.7 H | p | m |
| 4.3 to 4.4 | 2 H | 1.7 H | o | m |
| 4.4 to 4.6 | 1 H | 0.9 H | j | —$^{(2)}$ |
| 4.7 to 4.8 | 2 H | 1.7 H | n | d + d |

TABLE 2-continued (V)

$$CH_3-CH_2-(CH_2)_8-CH_2-CH_2-O-CH_2-CH_2-CH_2-\underset{H}{N}-\underset{\underset{O}{\|}}{C}-\underset{\underset{CH_2}{|}}{CH}-\underset{H}{N}-\underset{\underset{O}{\|}}{C}-\text{Fc}$$

$$CH_3-CH_2-(CH_2)_8-CH_2-CH_2-O-CH_2-CH_2-CH_2-\underset{H}{N}-\underset{\underset{O}{\|}}{C}-CH_2$$

a b c d e f g h i' l $^1$H-NMR assignment (250 MHz, organic gelling compound (III)/CDCl$_3$, 25° C., TMS)

| δ (ppm) | Theoretical Value | Observed Value | Assignment | Peak Splitting |
|---|---|---|---|---|
| 6.5 to 6.6 | 1 H | —(2) | i' | —(2) |
| 7.0 to 7.3 | — | — | i + CHCl$_3$ | — |
| 7.6 to 7.8 | 1 H | —(2) | m | —(2) |

Note:
(1)Reference value, and
(2)The integrated intensity cannot be evaluated, because a nitrogen nucleus has electric quadrupole moment providing a proton signal with large line width.

The product was further subjected to an elementary analysis. The results are shown in Table 3.

TABLE 3

| Results | Elementary analysis | | | |
|---|---|---|---|---|
| | H (%) | C (%) | N (%) | C/N |
| Observed | 9.68 | 68.07 | 5.15 | 13.21 |
| Calculated | 9.83 | 68.21 | 5.19 | 13.14 |

The above analysis confirmed that the ferrocene-containing, organic gelling compound (III), N-ferrocenyl-di(3-lauryloxypropyl)-L-glutamic acid, was synthesized.

EXAMPLE 2

Figure 4:
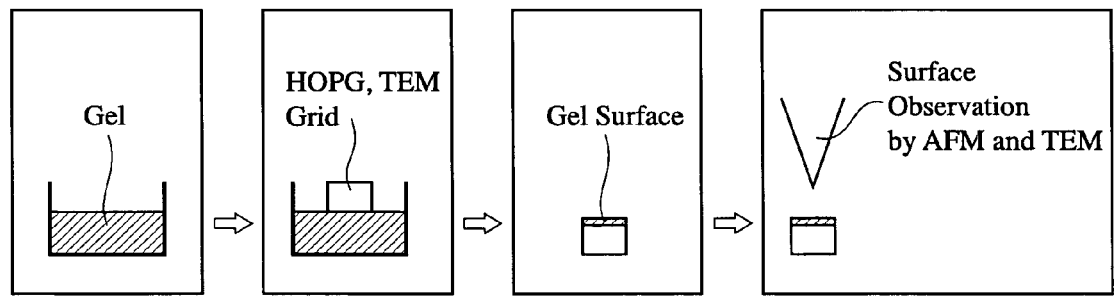
FIG. 4 is a flow chart showing gel transfer processes.
Figure 5A:
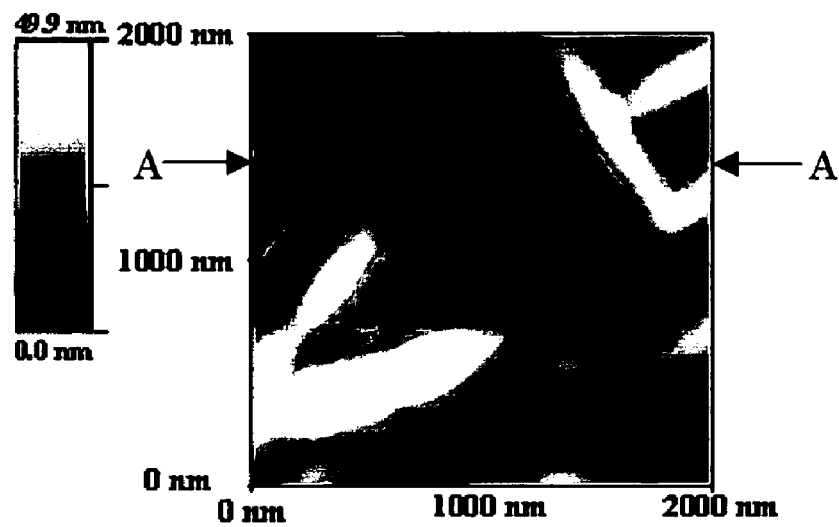
FIG. 5(a) is an atomic force photomicrograph of an acetonitrile gel produced by adding acetonitrile to the ferrocene-containing, organic gelling compound (III) at a concentration of 10 mM.
Figure 5B:
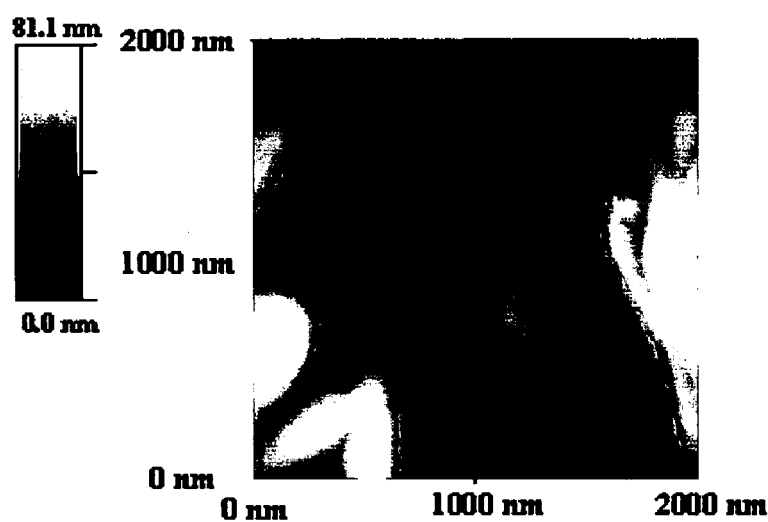
FIG. 5(b) is an atomic force photomicrograph of an acetonitrile gel produced by adding acetonitrile to the ferrocene-containing, organic gelling compound (III) at a concentration of 10 mM.
Figure 6:
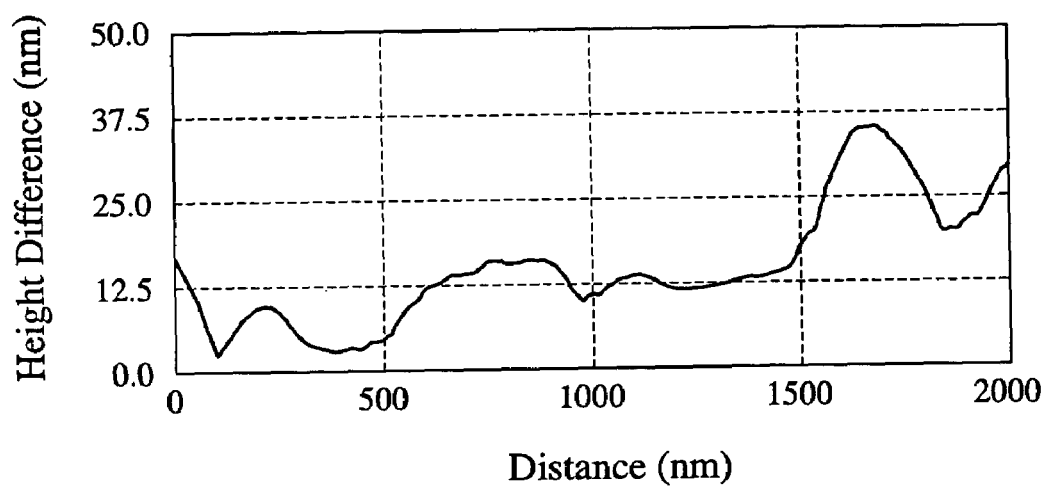
FIG. 6 is a graph showing surface raggedness in a section of the acetonitrile gel of FIG. 5(a) along the line A—A.
Figure 7A:
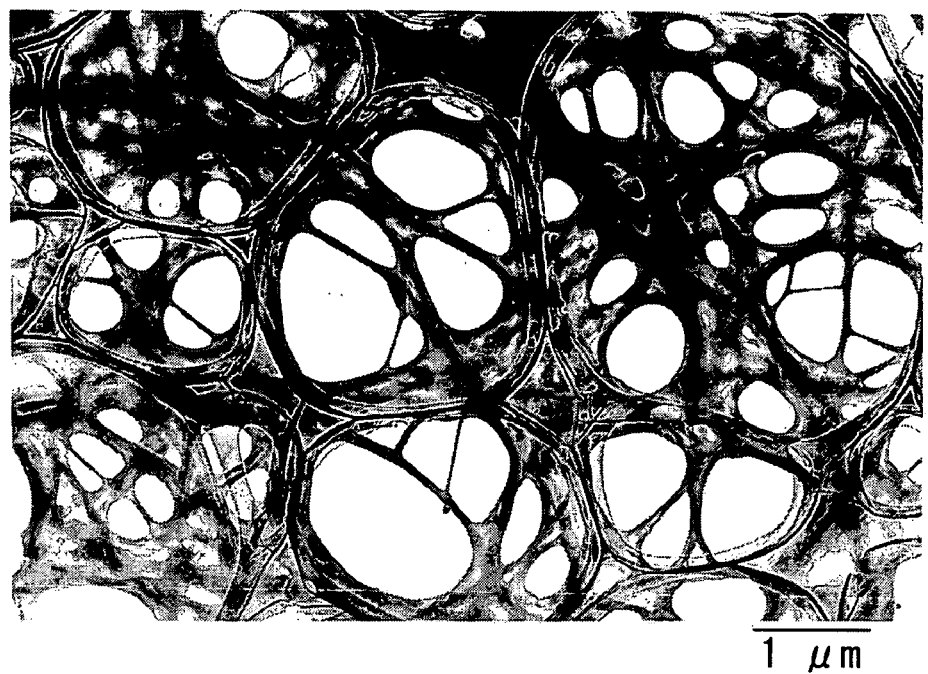
FIG. 7(a) is a transmission electron photomicrograph of the acetonitrile gel produced by adding acetonitrile to the ferrocene-containing, organic gelling compound (III) at a concentration of 10 mM.
Figure 7B:
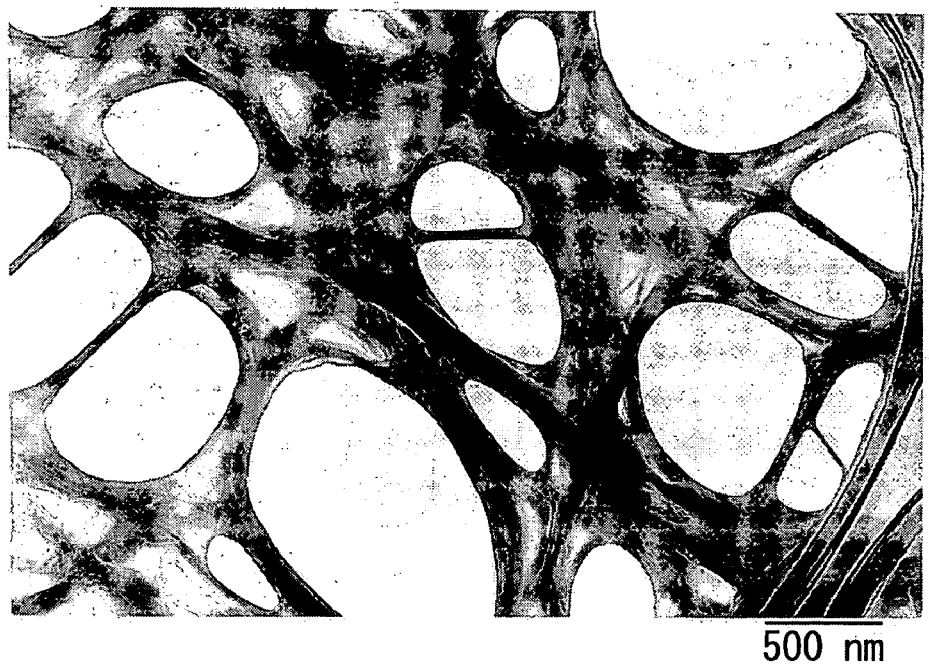
FIG. 7(b) is a transmission electron photomicrograph of the acetonitrile gel produced by adding acetonitrile to the ferrocene-containing, organic gelling compound (III) at a concentration of 10 mM.

The ferrocene-containing, organic gelling compound (III) produced in Example 1 (Mw 810, hereinafter referred to as the compound (III) unless otherwise stated) was dissolved in acetonitrile at a concentration of 10 mM while heating, and left to stand at room temperature for 30 minutes. The resultant organogel was transferred onto a highly oriented pyrolytic graphite (HOPG) substrate as shown in FIG. 4, air-dried, and then observed by an atomic force microscope (AFM). The results are shown in FIGS. 5(a) and 5(b). Roughness in a section of the organogel along the line A—A in FIG. 5(a) is shown in FIG. 6. The resultant organogel was transferred onto a TEM grid (a carbon-deposited mesh) as shown in FIG. 4, and then air-dried. A drop of a 2-weight-% aqueous tungsten phosphate solution was added to the organogel, and the resultant gel was observed by a transmission electron microscope (TEM). The results are shown in FIGS. 7(a) and 7(b). As shown in FIGS. 5 to 7, the organogel had a network structure of entangled fibers having diameters of 50 to 400 nm. It was clear that the network structure was impregnated and swelled with acetonitrile to form the organogel. It is considered that the network structure is a fibrous structure grown from a bilayer membrane of the ferrocene-containing, organic gelling compound (III).

EXAMPLE 3

Figure 8A:
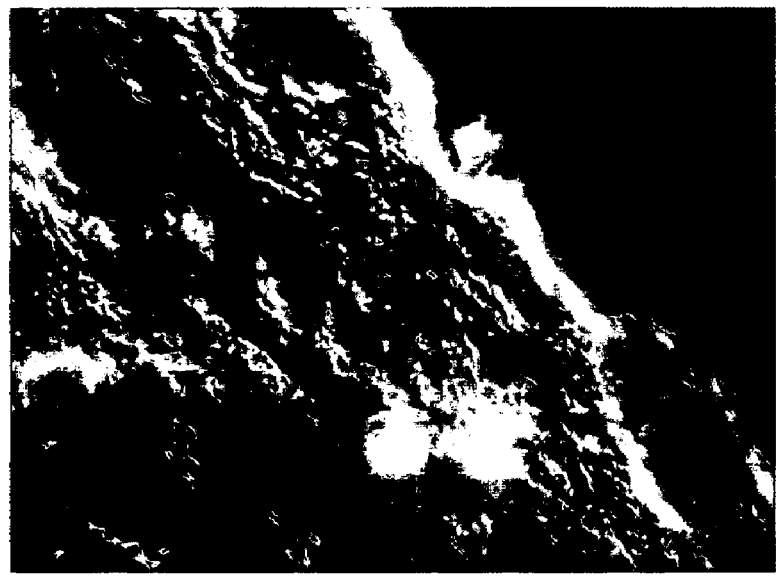
FIG. 8(a) is a dark-field optical photomicrograph of an acetonitrile gel produced by adding acetonitrile to the ferrocene-containing, organic gelling compound (III) at a concentration of 20 mM.
Figure 8B:
FIG. 8(b) is a dark-field optical photomicrograph of the acetonitrile gel produced by adding acetonitrile to the ferrocene-containing, organic gelling compound (III) at a concentration of 20 mM.

The ferrocene-containing, organic gelling compound (III) produced in Example 1 was dissolved in acetonitrile and N-methyl-N'-methoxymethylimidazolium bromide, respectively, at a concentration of 20 mM while heating, and left to stand at room temperature for 30 minutes, to produce an organogel and an ionogel, respectively. Each of the organogel and the ionogel was placed on a slide glass, and crushed with a cover glass. Observation by a dark-field optical microscope revealed that the organogel had a fibrous structure shown in FIG. 8(a) as in observation by AFM and TEM in Example 2. Microcrystals of the organogel were observed as shown in FIG. 8(b). It is not clear whether the existence of the microcrystals suggests that the microcrystals formed by the bilayer membrane of the organogel have an associated fibrous structure, or that an associated fibrous matter was crystallized when the organogel was crushed by the cover glass.

Figure 9:
FIG. 9 is a dark-field optical photomicrograph of an ionogel produced by adding N-methyl-N'-methoxymethylimidazolium bromide to the ferrocene-containing, organic gelling compound (III) at a concentration of 20 mM.

In the ionogel, an interface between a gel phase and an ionic liquid phase was observed as shown in FIG. 9. In FIG. 9, a cloudy portion represents the ionogel (the compound (III)+the ionic liquid), and a clear portion on the upper left represents the ionic liquid phase. A micron-level fibrous structure was not observed in the ionogel unlike in the case of the organogel. It is known that in gels formed by treating ionic liquids with conventional amphiphiles, bilayer membranes grow to fiber structures (JP 2002-265428 A, etc.). However, the ionogel comprising the compound (III) is not necessarily a fibrous aggregate, but the ionic liquid has remarkably increased viscosity in a portion (domain), in which the bilayer membrane microcrystals exist at a high concentration, resulting in the possibility that a gel is formed therein. Though a lot of circular matters like air bubbles were observed in the ionogel, their relation to the gelation is not clear.

EXAMPLE 4

Figure 10:
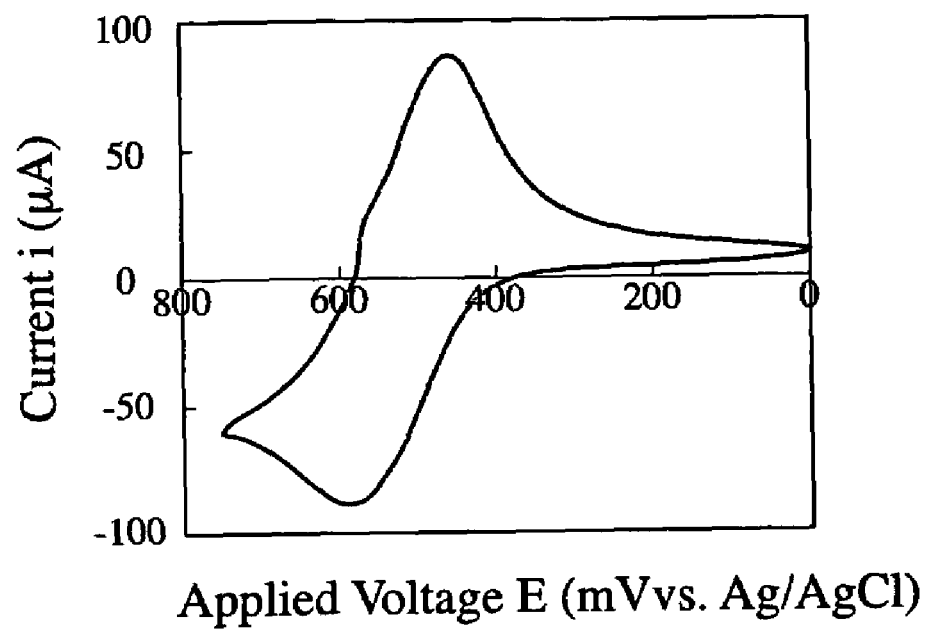
FIG. 10 is a cyclic voltammetry curve of a gel electrode comprising an ITO-coated substrate and an acetonitrile gel of the compound (III)

Acetonitrile and the ferrocene-containing, organic gelling compound (III) (concentration: 20 mM) produced in Example 1 were placed in a dish, and irradiated with ultrasonics by a probe sonicator to dissolve the compound (III). An ITO-coated substrate (60 Ω) was soaked in this solution, cooled with ice to form an organogel on the ITO-coated substrate, and cut to obtain an electrode. The redox properties of the organogel were evaluated by a cyclic voltammetry measurement at a sweep rate of 50 mV/s, using the resultant gel electrode [the ITO-coated substrate+the acetonitrile gel of the compound (III)] as an anode, a platinum electrode as a cathode, Ag/AgCl as a reference electrode, and a 0.5-M aqueous NaClO₄ solution as a supporting electrolyte. The resultant cyclic voltammetry curve (C-V curve) is shown in FIG. 10. It is clear from FIG. 10 that the organogel was excellent in redox properties.

EXAMPLE 5

Figure 11:
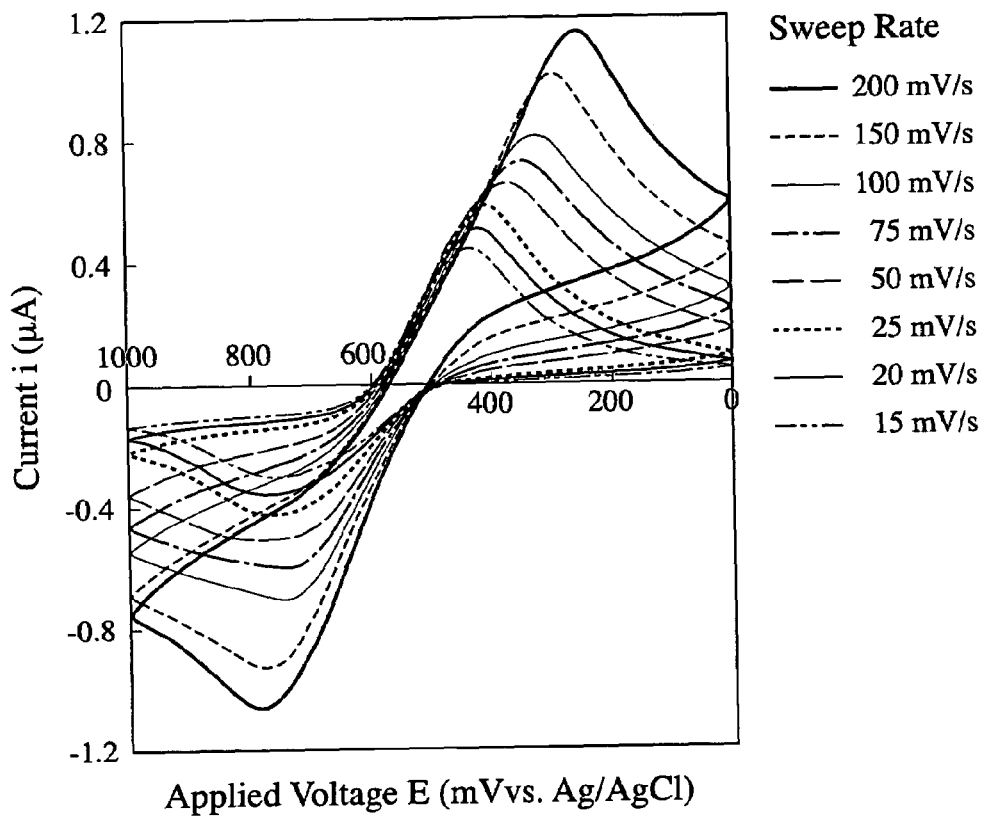
FIG. 11 is a cyclic voltammetry curve of a cast film electrode comprising an ITO-coated substrate and a cast film of the compound (III)

0.5 mL of a 0.5-mM solution of the ferrocene-containing, organic gelling compound (III) in methanol produced in Example 1 was divided to three and cast three times on an ITO-coated substrate (60 Ω) of 1.0 cm×3.0 cm, and air-dried to form a cast film of the compound (III) on the ITO-coated substrate. The redox properties of the cast film were evaluated by a cyclic voltammetry measurement at a sweep rate of 15 to 200 mV/s, using the resultant cast film electrode as an anode, a platinum electrode as a cathode, Ag/AgCl as a reference electrode, and a 0.5-M aqueous NaClO₄ solution as a supporting electrolyte. The resultant C-V curve is shown in FIG. 11. It is clear from FIG. 11 that the cast film of the compound (III) was excellent in redox properties.

Figure 12:
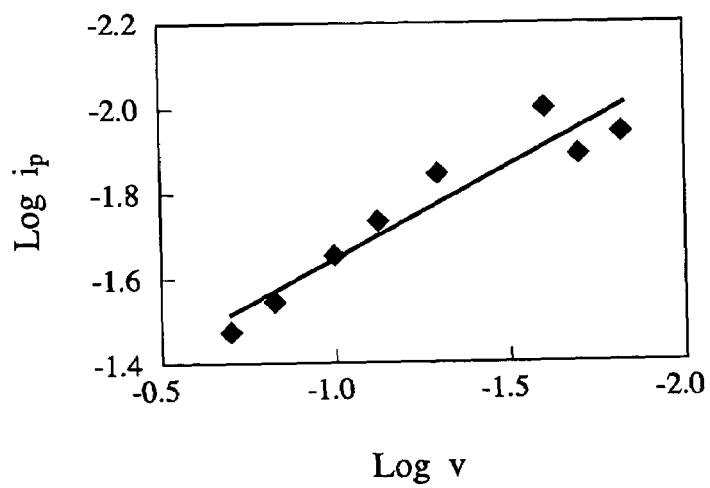
FIG. 12 is a logarithmic plot of peak current and sweep rate obtained from the cyclic voltammetry curve of FIG. 11.

Logarithmic plots of a peak current ($i_p$) and the sweep rate (v) obtained from the C-V curve of FIG. 11 are shown in FIG. 12. The form of electron transfer is generally evaluated based on the slope of the plots. It is presumed that the cast film comprising the compound (III) has such a structure that the alkyl chains of the compound (III) are adsorbed onto the ITO-coated substrate to form a monolayer membrane, and that a bilayer membrane is formed on the monolayer membrane. In this case, electrons may hop between the ferrocene groups to cause electron transfer in the cast film. It is thought that when voltage is applied to the cast film, the compound (III) molecules in the monolayer membrane are rotated such that the ferrocene groups face the ITO-coated substrate to achieve electron transfer. When the slope of the plots is 1.0, the molecules contributing to electron transfer with the ITO-coated substrate are adsorbed onto the ITO-coated substrate. When the slope of the plots is 0.5, the molecules contributing to electron transfer diffuse (or move) on an interface between the ITO-coated substrate and the cast film before and after the electron transfer. In the latter case, at least the monolayer membrane has a partly deteriorated structure. The slope of the plots in FIG. 12 is 0.44, suggesting that the molecules contributing to electron transfer with the ITO-coated substrate are diffused on the interface between the ITO-coated substrate and the cast film before and after the electron transfer.

Thus, the ferrocene-containing, organic gelling compound of the present invention can convert organic solvents and ionic liquids to gels, which can be used in various fields. Further, the ferrocene-containing, organic gelling compound of the present invention can be easily formed into a cast film having excellent redox properties on an electrode substrate.

APPLICABILITY IN INDUSTRY

As described above in detail, the ferrocene-containing, organic gelling compound of the present invention can convert particular organic solvents and ionic liquids to gels. The gels comprising the ferrocene-containing, organic gelling compound of the present invention have such excellent redox properties that they can be used for electrochemically controllable gel actuators, electrolyte layers of photoelectric conversion devices, redox layers of enzyme electrodes (immobilization layers of enzyme-immobilized electrodes), etc. The gel actuators are useful as artificial muscles for medical microsurgery apparatuses, micromachines of robots and motors, etc. Further, the ionogels prepared from the ionic liquids are promising as solid electrolytes in the field of batteries. Furthermore, the gels can be used as materials of light-driven gel actuators by adding photosensitizers such as ruthenium tris(bipyridine) complexes.

The ferrocene-containing, organic gelling compound of the present invention can be easily formed into a cast film on an electrode substrate. The cast film shows excellent redox properties, usable for intermediate layers between metal electrodes and ion-sensitive membranes, thin display devices, etc.

What is claimed is:

1. A ferrocene-containing, organic gelling compound represented by the following general formula (I):

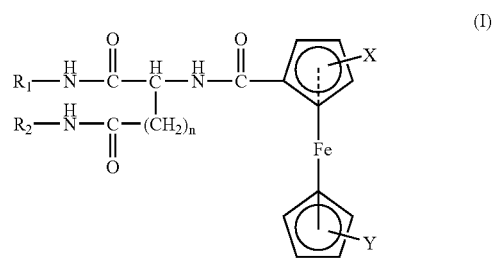

wherein $R_1$ and $R_2$ represent the same or different alkyl groups having 2 or more carbon atoms or alkyl groups containing at least one ether bond, X and Y independently represent a hydrogen atom or a substituent, and n represents an integer of 1 or 2.

2. The ferrocene-containing, organic gelling compound according to claim 1, wherein said gelling compound is represented by the following formula (II):

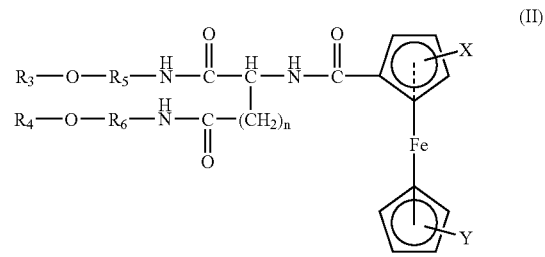

wherein $R_3$ and $R_4$ represent the same or different alkyl groups having 2 or more carbon atoms, $R_5$ and $R_6$ represent the same or different alkylene groups having 2 to 20 carbon atoms, X and Y independently represent a hydrogen atom or a substituent, and n represents an integer of 1 or 2.

3. The ferrocene-containing, organic gelling compound according to claim 1, wherein said gelling compound is represented by the following formula (III):

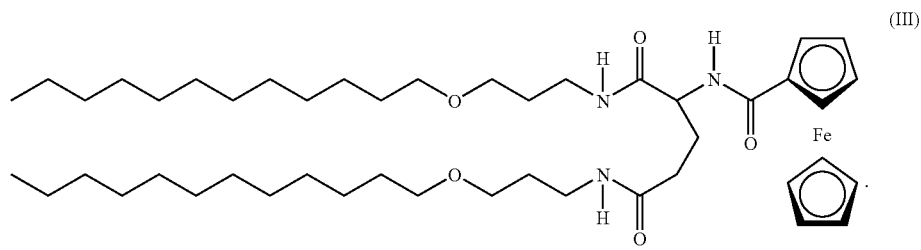

(III)

4. The ferrocene-containing, organic gelling compound according to claim 1, wherein said gelling compound can convert an organic solvent or an ionic liquid to a gel.

5. A gel comprising the ferrocene-containing, organic gelling compound recited in claim 1.

6. The gel according to claim 5, wherein said gel comprises said gelling compound and an organic solvent.

7. The gel according to claim 6, wherein said organic solvent is acetonitrile.

8. The gel according to claim 5, wherein said gel comprises said gelling compound and an ionic liquid.

9. The gel according to claim 8, wherein said ionic liquid is N-methyl-N'-methoxymethylimidazolium bromide.

10. A cast film obtained by casting the ferrocene-containing, organic gelling compound recited in claim 1.

* * * * *